United States Patent [19]

Rockett et al.

[11] 4,020,557

[45] May 3, 1977

[54] COMPOSITE FOR DENTAL RESTORATIONS

[75] Inventors: Thomas J. Rockett, East Greenwich, R.I.; John S. Tiffany, Camarillo; John J. O'Connell, Tustin, both of Calif.

[73] Assignee: American Hospital Supply Corporation, Evanston, Ill.

[22] Filed: Sept. 18, 1974

[21] Appl. No.: 507,223

Related U.S. Application Data

[63] Continuation-in-part of Ser. No. 416,808, Nov. 19, 1973, abandoned.

[52] U.S. Cl. .............................. 32/15; 260/42.15; 260/42.52; 260/998.11
[51] Int. Cl.$^2$ ...................... A61K 5/06; C08K 3/34
[58] Field of Search ....... 260/42.52, 998.11, 42.15; 32/15

[56] References Cited

UNITED STATES PATENTS

| | | | |
|---|---|---|---|
| 3,066,112 | 11/1962 | Bowen | 260/998.11 |
| 3,442,851 | 5/1969 | McManimie | 260/42.15 |
| 3,452,437 | 7/1969 | Chang | 32/15 |
| 3,520,949 | 7/1970 | Shepherd | 260/998.11 |
| 3,597,389 | 8/1971 | Taylor | 260/998.11 |
| 3,625,916 | 12/1971 | Newman | 260/998.11 |

OTHER PUBLICATIONS

*Handbook of Chemistry and Physics*, Chemical Rubber Pub. Co., 1959, pp. 2135 & 2136.

*Primary Examiner*—James H. Derrington
*Attorney, Agent, or Firm*—Tilton, Fallon, Lungmus, Chestnut & Hill

[57] ABSTRACT

An improved composite material for use as a dental restorative in which the major component consists of a finely-divided reinforcing filler having a hardness no greater than about 5.0 on the Moh's scale. Despite the relative softness of such a filler, in contrast to fillers conventionally used in dental composites, the final restoration has superior resistance to abrasion and wear, can be finished more effectively and more aesthetically, and can be handled with metal dental instruments.

9 Claims, 2 Drawing Figures

SURFACE CHARACTERISTICS OF POLISHED
PRIOR ART COMPOSITE

SURFACE CHARACTERISTICS OF POLISHED
COMPOSITE CONTAINING WOLLASTONITE FILLER

COMPOSITE FOR DENTAL RESTORATIONS

RELATED APPLICATION

This application is a continuation-in-part of copending application, Ser. No. 416,808, filed Nov. 19, 1973, abandoned.

BACKGROUND

The treatment prescribed by restorative dentistry for a carious lesion of the enamel or dentin is simply to cut out the affected tissue with a drill. The cavity produced must then be filled in order to restore the strength of the tooth, protect the adjacent tissue from further decay and thermal shock, and, especially in the anterior teeth, restore the natural appearance of the tooth. To fill such a hole, the dentist has several methods at his disposal. All of the techniques have certain advantages and disadvantages but none has all of the properties which Black in 1895 outlined for the ideal restorative material (G. V. Black, "An Investigation of the Physical Characters of the Human Teeth in Relation to their Disease, to Practical Dental Operations, Together with the Physical Characters of Filling Materials," Dent. Cosmos., Vol. 37). Since 1915, silicate cements have been the major material for aesthetic restorations (C. C. Volker, "Dental Silicate Cements in Theory and Practice," Dent. Cosmos. Vol. 58, 1098 (1916)). Such a material has three major weaknesses; it has a high solubility and therefore is subject to wash-out which causes its poor long-term stability, it loses its aesthetic properties by discoloration caused by absorption of oral fluids, and it is a highly brittle material which cannot be used on stress bearing surfaces. Efforts to develop a better material led to the introduction of direct filling resins in the late 1940's. Excessive polymerization shrinkage and poor thermal expansion characteristics were the major weaknesses of these materials. Also, the prevalence of recurrent caries produced by oral fluid ingress along marginal gaps between the restoration and the tooth caused by excessive shrinkage in setting contraindicated continued use of such materials (F. A. Peyton, et al, "Restorative Dental materials," C. V. Mosby, St. Louis, p. 465 (1964)). Painstaking implacement of these materials by slow build-up of the restoration in thin layers did produce excellent restorations. Wear and wash-out were never considered problematic, but the slow procedure took hours and the resultant cost was prohibitive for the patient.

In recent years a new class of materials has been introduced which is regarded as offering more advantages than any of the earlier efforts, namely, ceramic reinforced polymer matrix composites ("Guide to Dental Materials and Devices," 4th Ed., Amer. Dent. Assoc., Chicago (1968)). Such materials were developed largely through the efforts of R. L. Bowen and are now being widely marketed for use as both anterior and posterior restorative materials.

The composites involve a methacrylate based system in which a silica or silicate glass filler is covalently bonded to a resin matrix, or to a coupling agent which is covalently bonded to both. With fillers used to the 70—80 weight percent level, polymerization shrinkage and thermal expansion are greatly reduced in comparison with direct filling resins. The problems with recurrent caries which was observed in connection with the use of the earlier direct filling resins appears non-existent with the use of the dental composites. In terms of stability, solubility, strength, and general performance, the ceramic reinforced polymer matrix composites overcome many of the objections raised with regard to the earlier silicate cements and direct filling resins.

Despite their advantages, such composites have not been entirely satisfactory from the standpoint of resistance to abrasion and wear, ease of finishing and ease of implacement. The greater hardness of the glass or mineral particles (all of which range from 5.5 to 7.0) relative to the hardness of tooth enamel would be expected to result in restorations of high durability and retentiveness but, contrary to such expectations, and as set forth hereinafter, applicants have now found that such hardness is actually a disadvantage rather than an advantage in several respects.

Other patents and literature showing the state of the prior art are Bowen U.S. Pat. Nos. 3,066,112, 3,200,142 and 3,635,889, Chang U.S. Pat. No. 3,452,437, and the references cited therein; Bowen, R. L. et al, "Composite Restorative Materials," paper given at 50th Anniversary Symposium on Dental Material Research, NBS, Oct. 6–8, 1969; L. J. Brontman et al, "Modern Composite Materials," Addison-Wesley Publishing Co., Reading, Mass. (1967); R. L. Bowen, "Effect of Particle Shape and Size Distribution in a Reinforced Polymer," J. ADA, Vol. 64, p. 481 (1964); W. Souder et al, "Physical Properties of Dental Materials," National Bureau of Standards Circular C433, U.S. Government Printing Office, Washington, D. C. (1942).

SUMMARY

An important aspect of the present invention lies in the discovery that a dental restorative material possessing all of the advantages of conventional composites but with increased durability, improved workability, and improved finishing characteristics is obtained by using a relatively soft filler having a hardness of at least 3.0 but no greater than about 5.0 on the Moh's scale of hardness, as contrasted with using a conventional crystalline silica filler, or silicate glass filler, having a hardness of 5.5 or greater. While it might be thought that the wearing properties of a composite formed with a relatively hard filler of 5.5 or more would be superior to those of a composite having a filler with a hardness of approximately 4.5, we have found that the harder particles actually tend to be released by or plucked out of the polymer matrix as the matrix itself becomes worn and that the microscopic cavities caused by loss of the hard filler particles present new and irregular sites for further wear and result in a dull and unpleasing appearance and feel. Furthermore, the plucking out of such grains places coarse and abrasive wear debris at the interface between a restoration and an adjacent tooth. Such loose interfacial debris can cause wear of the tooth and the restoration as the teeth move past one another during mastication. By contrast, a softer filler material, especially one which is capable of being securely bonded or coupled to the resin matrix, which itself has a hardness within the range of 2.0 to 4.0, tends to wear evenly with the matrix material and therefore resists the plucking action, and gives rise to a composite which has superior wear characteristics, in that the surface stays continuously smooth and aesthetically more pleasing than the rough, plucked surface. Furthermore, it has been found that the compressive strength of a dental composite material formed with a relatively soft inorganic filler such as wollastonite is about equal to that of a composite made with a hard glass or mineral filler. While the reasons for the surprisingly high compressive strength of the polymer-wollastonite composite are not fully known, the high strength of the bond between the resin and filler is believed to be of considerable significance. Another feature of the improved wear characteristics is the increased ease of finishing. Most composite restorations are over-filled and after setting must be ground to match the tooth contour. This grinding is done using a diamond wheel. During grinding, considerable plucking takes place if the filler is hard. The irregular surface produced is rough in contact with the tongue, dull in appearance and can discolor by food debris packing in the irregular surface in extreme cases.

Since the fillers used in a composite embodying the present invention have a hardness within the range of 3.0 to 5.0, their hardness does not exceed that of the metallic tools commonly used by a dentist in forming restorations. The significance of that advantage is substantial; in the use of prior composites, dentists have been cautioned to use special tools or special techniques to prevent any abrasion of metal surfaces that might cause microscopic particles of metal to remain with the composite and discolor the restoration. Even minute amounts of metal abraded from such tools by the filler particles may cause highly objectionable discoloring or darkening of a restoration. Since the composites are extremely stiff, mixing with plastic or agate tools often leads to breakage of the instruments. The use of stronger metal tools allows for more uniform mixing and therefore a better restoration.

Other objects, aspects, and advantage of the invention will become apparent as the specification proceeds.

DRAWINGS

DETAIL DESCRIPTION

Figure 1:
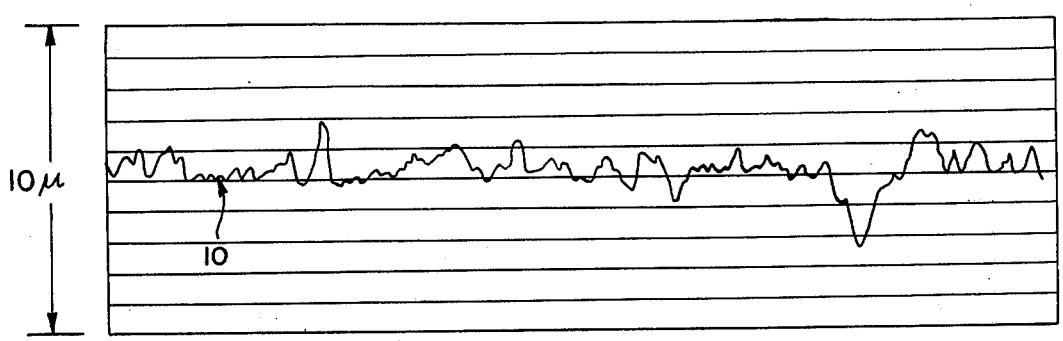
FIG. 1 is a graph illustrating the surface characteristics (roughness) of a conventional dental restorative material after the cured surface was polished with a conventional diamond bur.

As already indicated, this invention is believed useful in conjunction with any of the standard polymeric binders used for preparing dental composites, such binders all being methacrylate based having refractive indices within the range of 1.53 to 1.56, and being of a hardness within the range of 2.0 to 4.0 Mohs. For that reason, and because information concerning the formulation and preparation of such binders, and the coupling agents used therewith, is well known and readily available, as indicated by the citations already given, a detailed description of the binder system is believed unnecessary herein. In general, it may be stated that most commercially available dental composite resins are based on a dimethacrylate-monomethacrylate comonomer system. A typical formulation would contain a crosslinking dimethacrylate monomer (such as the monomeric reaction product of 4,4'-isopropylidenediphenol and glycidyl methacrylate commonly called BIS-GMA), in conjunction with a comonomer for reducing the viscosity of the liquid phase, suitable polymerization accelerators, color stabilizers, and polymerization inhibitors. As a viscosity-reducing comonomer, methylmethacrylate or ethyleneglycol dimethacrylate may be used. The accelerator system may be composed of co-catalysts such as benzyl peroxide and an aromatic tertiary amine. Stabilizers, which act as free radical traps and inhibit the premature polyermization of the methacrylate monomers, may be hydroquinone, or substituted hydroquinones, or a hindered phenol such as 2,6,-di-tert-butyl-p-cresol. Finally, a silane coupling agent, such as trialkoxysilanes containing an organic function, may be used to promote adhesion between the binder and the filler material in a manner as fully disclosed in the prior art. It is to be understood, however, that the use of a silane coupling agent may not be necessary or even desirable in all cases and that techniques are available, or may become available, for the direct bonding of the filler to the polymeric matrix.

The filler is a non-toxic inorganic compound, either crystalline or amorphous, which is capable of being finely divided, takes the form of a whitish powder, is substantially insoluble in water, and has a hardness within the range of 3.0 to 5.0 on the Moh's scale of hardness, the preferred hardness being substantially less than 5.0 (i.e., about 4.5). Minerals suitable for the purpose may consist of calcium silicates such as wollastonite, $CaO.SiO_2$, datolite, $Ca(B,OH)SiO_4$, and tremolite, $CaMg_3(SiO_4)_3$, other silicates such as hemimorphite, $2ZnO.SiO_2.H_2O$, apophylite $K_2O.8CaO.16SiO_2.16H_2O$, and clinoenstatite, $MgO.SiO_2$, or phosphates such as whitlockite, $Ca_3(PO_3)_2$, para hopeite, $Zn_3(PO_4)_2.4H_2O$, and fluoroapatite, $CaF_2.3Ca_3P_2O_8$. Any glass, as long as it meets the above requirements and, in particular, has a hardness within the range of 3.0 to 5.0 may be used.

The filler material may be reduced to microparticle size, approximately 30 microns or less, by ball milling or by any other suitable grinding or milling procedure. All impurities or contaminants should be avoided or removed from the powder. Thereafter, the particles may optionally be coated with a suitable coupling agent as indicated above and as fully disclosed in the prior art of record. In use, the filler powder may be mixed directly with the polymeric binder and catalyst heretofore described, and the mixture may then be placed into the cavity to be filled where it quickly hardens (within about 10 minutes) by polyermization of the organic material. To facilitate handling of the materials at the time of the final mixing, the ingredients may be premixed and marketed as two mixtures of paste, each mixture containing the desired proportion of filler and resin, or as a paste which is set using a liquid catalyst. One of the mixtures would then contain one component of the cocatalyst system (such as benzyl peroxide) and the other mixture would contain the other component (accelerator) of that system (such as an aromatic tertiary amine).

In either case, the filler constitutes the major component of the composite material, constituting at least 70 percent, and preferably 75 to 80 percent, by weight, of the total composite.

The minerals identified above as fillers suitable for use in preparing composites embodying the invention are characterized by having relatively high refractive indices falling generally within the range of 1.60 to 1.66. Other materials, such as the silicate glass also identified above, have indices of refraction closer to that of the resin binder (about 1.55). Matching the refractive indices of the binder and filler produces a composite having a higher degree of translucency. It is significant, however, that the greater opacity arising from a substantial mismatch between the refractive indices of the binder and filler materials results in a composite which is aesthetically superior for many applications. It has been found that the line of demarcation between the surface of a restoration and a natural tooth surface is more difficult to distinguish or detect visually, especially where the restoration is deep and applied to the lower portion or face of a tooth, if the cured composite material is more opaque. Consequently, the use of a filler having a relatively high index of refraction has been found to be advantageous rather than disadvantageous in many applications.

Wollastonite, having an average refractive index of 1.63 (it is anisotropic, having 3 indices of refraction at 1.610, 1,611, and 1.66) has been found particularly effective for use as a filler material. It has substantially the same hardness as tooth enamel (4.5) and may be securely bonded to the resin matrix with the use of a silane coupling agent. Because of the mismatch between the average refractive index (1.63) of wollastonite and the refractive index of the resin binder (about 1.55), a relatively opaque composite is formed.

Despite its important advantages, wollastonite in its natural form has physical characteristics which tend to limit the proportional amount of such filler that may be mixed with the resin. It has been found that the fibrous crystals of natural wollastonite (form A), tend to stack upon each other in a manner that limits the amount of filler to under 70 percent. Grinding, in order to reduce particle size and increase packing, does not effectively solve the problem because the crystals shear longitudinally, retaining their fibrous form. To overcome such problems, pseudowollastonite (form B) may be prepared by reacting sodium metasilicate with calcium chloride to produce an amorphous precipitate of calcium silicate. After thorough washing, the precipitate is fired to approximately 1450° C., just below the melting point of wollastonite but above the temperature (1150° C.) at which a transition occurs from form A to form B. The wollastonite (or pseudowollastonite) is then quenched and the material in its B phase is milled until the particles are of a size below 30 microns in size.

The result is a synthesized wollastonite or pseudowollastonite in the form of a fine powder which is similar to natural wollastonite except that grinding does not produce particles which are fibrous. Because of the non-fibrous nature of the particles, filler loadings of 70 to 80 percent are possible. When mixed with the resin binder, the result is a superior dental composite having relatively high compressive strength and having the other characteristics described.

The hardness of standard polymeric binders on the Moh's scale of hardness falls within the range of 2.0 to 4.0, most commonly between 2.3 and 3.2. A dental composite formulated with such a binder and the "soft" (3.0 to 5.0) inorganic fillers described above has been found capable of being polished to a relativey smooth surface in comparison with composites prepared with harder (5.5–7.0) conventional silica or silicate glass fillers. Such greater smoothness is believed to be related to the superior wearing properties of the present composites since the forces applied during polishing, as well as during normal wear, are believed to be distributed over a greater surface area than would otherwise occur. Stated differently, it has been found that in prior composites the difficulty in achieving a smooth polished surface has arisen because of the hardness and strength of the filler particles. The energy required to fracture such particles (whether by polishing or by normal wear) is much greater than the energy required to break the resin-filler bonds. The concentration of forces on exposed particles of relatively hard conventional fillers tends to cause such particles to be plucked or extracted from the resin matrix, leaving an irregular resin surface which, upon continued exposure to polishing or wearing forces, is readily abraded until the forces are again concentrated upon a filler particle which is similarly plucked out or dislodged, and so the process continues. On the other hand, with a restoration formed with a composite embodying the present invention, utilizing a filler having a hardness within the range of 3.0 to 5.0, the grinding or wearing forces are more evenly distributed over a greater area, the plucking or dislodging of filler particles is eliminated or greatly reduced, and the polishing and wearing properties of the composite are substantially improved. Such improvement is readily discernible by comparing the smoothness of such a restoration, after it has been polished, with a restoration prepared with a conventional composite which has been identically treated.

During grinding or wear of a composite, if the included filler particles are soft enough so that they are worn down evenly with the matrix resin, the material surface is therefore continually kept smooth. Only when the filler is much harder than the resin does the resin dish out, exposing filler grains. The protruding grains act as stress concentrators and become plucked out. Further, the presence of hard wear debris at an interface increases wear on the surfaces. If surfaces can be kept smooth during interaction, relatively little wear takes place.

The invention may be more fully understood by the following illustrative examples:

EXAMPLE 1

A dental composite in which the filler material is pseudowollastonite (synthesized), having a hardness of about 4.5 Mohs, may be prepared as follows:

Dissolve 212.15 gms. sodium silicate in 3000 ml distilled water and mix with a solution of 111.00 gms. calcium chloride dissolved in 750 ml distilled water to form an amorphous precipitate of calcium silicate. After being washed and dried, the precipitate is placed in a platinum-lined crucible, heated to a temperature of 1400° to 1425° C. for 45 minutes, quenched in cold water, and then thoroughly dried. The pseudowollastonite is then ground in a ball mill for several days until the average particle size is well under 30 microns.

A silane solution for treating the filler is prepared by mixing 4.0 gms. of t-methacryloxy propyl trimethoxy silane, 180 gms. (228 ml) methanol, and 20 gms. distilled water. 400.0 gms. of the wollastonite powder is then added to the silane solution and is thoroughly mixed therewith. The mixture is then placed in an oven, heated to 65° C. to evaporate excess liquid, and thereafter heated at 110° C. for 2 hours. After washing with acetone, the treated filler is dried in an oven at 110° C.

The resin to be used as a binder may be prepared by mixing 1.5 gms. Permasorb MA, 70.0 gms. BIS-GMA, 15.0 gms. trimethylol propane trimethacrylate, 15.0 gms. ethylene glycol dimethacrylate, and 0.05 gms. 2,5-di-t-butyl-p-cresol (BHT), heating gently until a homogeneous mixture is formed. Equal amounts of the base resin may then be mixed with correspondingly equal amounts of the treated filler to produce a two component system, to one of which is added a catalyst and to the other of which is added an accelerator.

Part A of the two component system is prepared by first mixing 1.8 gms. benzoyl peroxide (catalyst paste)

and 45.0 gms. of the base resin and then, after a homogeneous mixture is formed, slowly adding with continual mixing 180 gms. of the treated filler powder. Mixing is continued until a homogeneous paste is formed.

Part B of the system is prepared by first mixing 0.675 gms. m-tolyl diethanolamine and 45 gms. of the base resin until a homogeneous mixture is formed, and then slowly adding (with continuous mixing) 180 gms. of the treated filler powder. Mixing is continued until a homogeneous paste is formed.

EXAMPLE 2

A composite prepared in accordance with Example 1 was used to make a series of dental restorations on human patients and was also used to prepare sample chips on which comparative tests were run. The final step of preparing the composite was undertaken by mixing equal quantities of parts A and B. In making the restorations, standard stainless steel tools were used to force the paste mixture into the prepared cavities and to smooth the surfaces of the restorations after the composite had fully cured. Thereafter, the restorations were finished using a conventional dental handpiece with a diamond disc.

The composite was more easily worked than conventional dental composites because standard stainless steel tools (not usable with conventional composites because of metal abrasion) could be used. Although the new composite material produced a restoration more opaque than conventional composites, the results were deemed highly effective and were observed to be aesthetically superior on specific tooth surfaces where the lines of demarcation between the restoration and the natural tooth surface were virtually if not completely undetectable to the naked eye.

Curing times fell within the range of 3 to 8 minutes, depending partly on ambient temperature. Compressive strength tests on the chips yielded results of 42,800 psi. Water solubility at 100° C. for 72 hours was found to be 0.7 percent, and water adsorption at the same temperature and interval was found to be 0.6 percent. Ultraviolet exposure tests, conducted by exposing the chips to light from a high intensity ultraviolet light source disposed 45 centimeters from the samples for a period of 12 hours failed to reveal any detectable yellowing of the samples when compared with chips not exposed to the ultraviolet light source.

EXAMPLE 3

Figure 2:
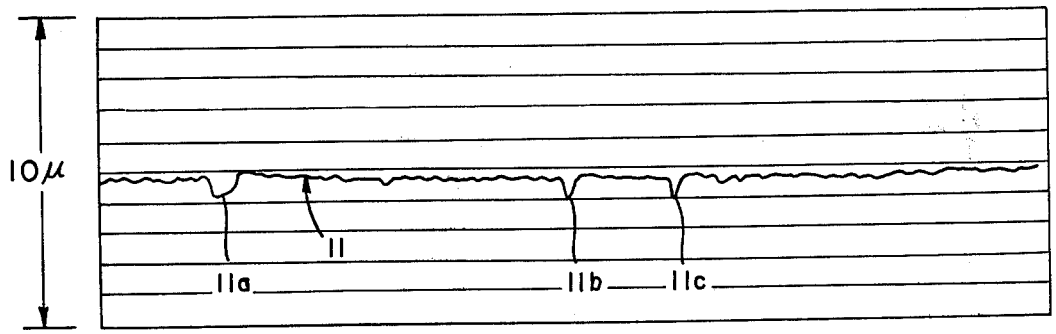
FIG. 2 is a similar graph illustrating the results obtained when a composite embodying the present invention was subjected to the same treatment.

Composite chips prepared in accordance with Examples 1 and 2 were subjected to smoothness tests utilizing a roughness testing device. The device included a stylus mounted to detect microscopic irregularities in the surface and connected to a recorder capable of graphically recording stylus deflections. The total distance of longitudinal movement over the surface of each chip was 4 millimeters. FIGS. 1 and 2 illustrate the results obtained when chips composed of a dental restorative prepared in accordance with Examples 1 and 2 (FIG. 2) were compared with chips prepared using a conventional restorative material containing silica as the filler material, the latter being marketed under the proprietary name "Adaptic" (FIG. 1).

All chips were prepared in the same manner except that plastic tools were required for smoothing the surface of the Adaptic material prior to setting because the abrasive action on stainless steel tools was found to produce discoloration. After hardening, the surfaces of all chips were exposed to the same polishing technique using a diamond disc. The stylus was then moved 4 millimeters along the polished surfaces of the respective chips to produce the graphs of FIGS. 1 and 2.

The maximum vertical distance depicted in each graph is 10 microns. Line 10 in FIG. 1 illustrates the movement of the stylus, the extent of roughness being represented by the maximum range of deflection of the needle and measuring approximately 4.5 microns. Line 11 in FIG. 2 reveals a maximum deflection of approximately 1.0 microns. Microscopic examination of the chips revealed that the roughness represented by line 10 was primarily the result of the extraction or plucking out of silica particles from the resin matrix during the polishing operation, leaving voids or recesses, and in some instances upstanding projections, in the resin matrix. Similar microscopic examination of the composite of FIG. 2 revealed that the largest recesses or depressions (which were still no more than 1 micron in depth) were the result of air pockets later exposed by the polishing operation. There was no evidence of soft silicate glass particles having been dislodged or plucked out of the resin mixtrix during the grinding operation and, except for the occasional irregularities 11a–11c produced by exposure of air pockets, the surface variations, as depicted in FIG. 2, were substantially less than 0.5 microns.

EXAMPLE 4

Composites embodying the invention are prepared using the resin binder, catalyst and accelerator and applicable procedure of Example 1, but with a finely-ground (average particle size below 30 microns) filler, in an amount sufficient to achieve a loading by weight of approximately 75 to 85 percent, of any of the following:

$K_2O.8CaO.16SiO_2.16H_2O$ (apophylite)
$Ca(B,OH)SiO_4$ (datolite)
$CaMg_3(SiO_4)3$ (tremolite)
$2ZnO.SiO_2.H_2O$ (hemimorphite)
$Ca_3(PO_3)2$ (whitlockite)
$CaF_2.3Ca_3P_2O_8$ (fluoroapatite)

As set forth in Example 1, a two-component system is prepared in which Part A and Part B contain equal amounts of filler and equal amounts of resin, the resin and filler of each component being intimately mixed to form a homogeneous paste. One component also contains the catalyst of Example 1, the other contains the accelerator identified in that example. Upon mixing equal quantities of the two components, a composite is formed which may be easily worked and smoothed with conventional stainless steel tools and upon curing may be polished to provide a relatively smooth and highly wear resistant surface substantially free of recesses or depressions caused by the separation and release of filler particles from the resin matrix. Abrasive forces applied to such a cured composite cause substantially equal and simultaneous wear of both the filler and resin constituents.

While in the foregoing we have disclosed embodiments of the invention in considerable detail for purposes of illustration, it will be understood that many of those details may be varied without departing from the spirit and scope of the invention.

We claim:

1. A method for preparing a dental restoration, comprising the steps of mixing and chemically coupling (a) a non-toxic and substantially waterinsoluble inorganic compound having a hardness within the range of 3.0 to about 4.5 Mohs and in the form of a powder having finely-divided particles of an average size less than 15 microns with (b) minor proportion of a methacrylate polymeric resin binder having a refractive index within the range of 1.53 to 1.56 and having a hardness when cured within the range of 2.0 to 4.0 Mohs, said inorganic compound being selected from a group consisting of silicates and phosphates of crystalline and amorphous form, and thereafter applying the mixture to a site requiring dental restoration.

2. The method of claim 1 in which said inorganic compound is wollastonite.

3. The method of claim 1 in which said inorganic compound is whitlockite.

4. The method of claim 1 in which said inorganic compound is hemimorphite.

5. The method of claim 1 in which said inorganic compound is clinoenstatite.

6. The method of claim 1 in which said inorganic compound is fluoroapatite.

7. The method of claim 1 in which said inorganic compound is apophylite.

8. The method of claim 1 in which said inorganic compound is pseudowollastonite in crystalline form prepared by first heating precipitated calcium silicate to a temperature in excess of 1150 degrees C. to form pseudowollastonite having non-fibrous crystals and then quenching and grinding said pseudowollastonite to a finely-divided powder.

9. A method for preparing an improved composite material for use as a dental restorative, comprising the steps of heating precipitated calcium silicate to a temperature in excess of 1150° C. to form pseudowollastonite having non-fibrous crystals, then quenching and grinding said pseudowollastonite to a finely-divided powder, and thereafter mixing and coupling said finely-divided powder with a minor proportion of a methacrylate polymeric resin binder having a refractive index within the range of 1.53 to 1.56.

* * * * *